(12) United States Patent
Shah et al.

(10) Patent No.: US 9,333,337 B2
(45) Date of Patent: May 10, 2016

(54) METHOD OF FABRICATING HIGH-DENSITY HERMETIC ELECTRICAL FEEDTHROUGHS USING INSULATED WIRE BUNDLES

(75) Inventors: Kedar G. Shah, Oakland, CA (US); William J. Benett, Livermore, CA (US); Satinderpall S. Pannu, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 197 days.

(21) Appl. No.: 14/118,183

(22) PCT Filed: May 16, 2012

(86) PCT No.: PCT/US2012/038216
§ 371 (c)(1),
(2), (4) Date: Jan. 14, 2014

(87) PCT Pub. No.: WO2012/158845
PCT Pub. Date: Nov. 22, 2012

(65) Prior Publication Data
US 2014/0144694 A1 May 29, 2014

Related U.S. Application Data

(60) Provisional application No. 61/486,636, filed on May 16, 2011.

(51) Int. Cl.
*A61N 1/05* (2006.01)
*A61N 1/375* (2006.01)

(52) U.S. Cl.
CPC ............... *A61N 1/05* (2013.01); *A61N 1/3754* (2013.01); *Y10T 29/49194* (2015.01)

(58) Field of Classification Search
CPC ............................... A61N 1/05; A61N 1/3754
USPC ............................................. 174/650; 29/868
See application file for complete search history.

(56) References Cited

U.S. PATENT DOCUMENTS

2006/0070887 A1* 4/2006 Zdeblick et al. ............... 205/652
2009/0187229 A1* 7/2009 Lavie ............................... 607/36
2013/0100595 A1* 4/2013 Koester et al. ........... 361/679.01

FOREIGN PATENT DOCUMENTS

GB          1005311      * 9/1965

* cited by examiner

*Primary Examiner* — Timothy Thompson
*Assistant Examiner* — Charles Pizzuto
(74) *Attorney, Agent, or Firm* — James S. Tak (57) ABSTRACT

A method of fabricating electrical feedthroughs coats of a plurality of electrically conductive wires with an electrically insulating material and bundles the coated wires together in a substantially parallel arrangement. The bundled coated wires are secured to each other by joining the electrically insulating material of adjacent wires together to form a monolithic block which is then cut transverse to the wires to produce a block section having opposing first and second sides with a plurality of electrically conductive feedthroughs extending between them.

13 Claims, 7 Drawing Sheets

METHOD OF FABRICATING HIGH-DENSITY HERMETIC ELECTRICAL FEEDTHROUGHS USING INSULATED WIRE BUNDLES

CROSS-REFERENCE TO RELATED APPLICATIONS

This patent document claims the benefits and priorities of U.S. Provisional Application No. 61/486,636, filed on May 16, 2011, hereby incorporated by reference.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

TECHNICAL FIELD

This patent document relates to methods of fabricating hermetic electrical feedthroughs, and in particular to a method of fabricating high-density hermetic electrical feedthroughs using insulated wire bundles.

BACKGROUND

Figure 1:
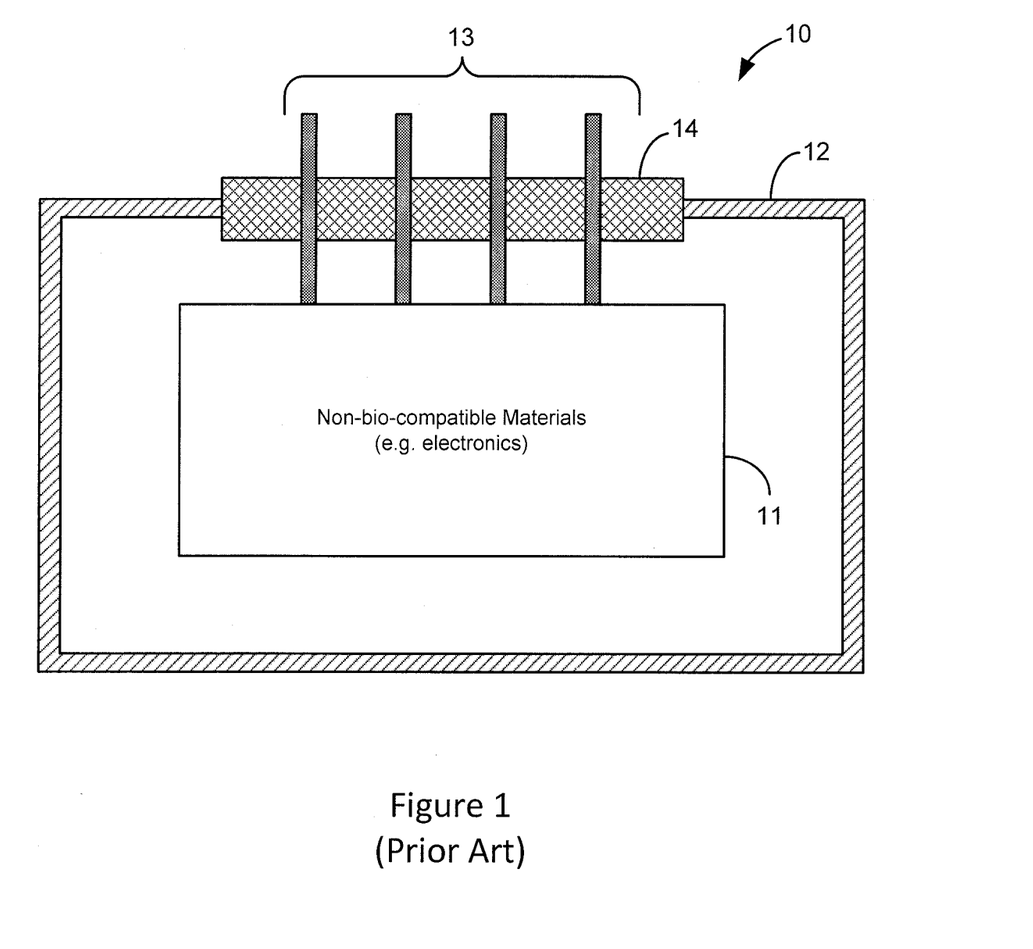
FIG. 1 is a schematic view of an implantable device illustrating a common approach to encapsulating non-bio-compatible component materials in a bio-compatible sealed package.

Electrically-active implantable bio-medical devices (such as for example pacemakers, cochlear implants, and neural prosthetics) are increasing in popularity due to the potential of continuous monitoring, instantaneous and directed delivery of treatments, reduction of treatment costs, and unique treatment options. However, because many of the component materials used in such devices are not bio-compatible, that is, they are toxic to the body and can induce undesirable biological reactions, it is critical to hermetically seal the non-bio-compatible components (e.g. CMOS, passive components, batteries) in a bio-compatible material, so that the body does not have a cyto-toxic response. Hermetic sealing also helps protects electrical components from damage due to moisture and the corrosive environment in the body. FIG. 1 shows a schematic illustration of a common hermetic encapsulation approach for implantable devices, such as 10, where non-bio-compatible components and materials 11, such as electronics, are encapsulated in a hermetically sealed package 12 made of bio-compatible materials. In this arrangement, an array of hermetic electrically conducting feedthroughs 13 is provided on an electrically insulating portion 14 of the package 12 for use as electrical conduits which allow communication of electrical signals between the body and electronics within the package.

Figure 2A:
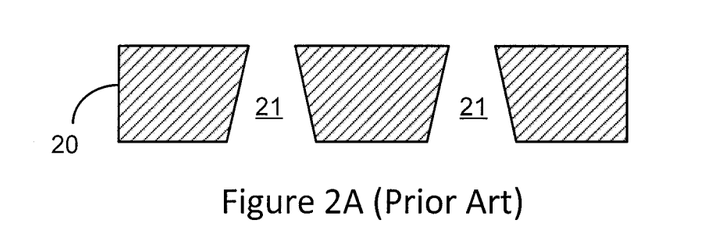
FIG. 2A is a cross-sectional view of a substrate with holes produced by laser cutting in a first example method of fabricating feedthroughs known in the art.
Figure 2B:
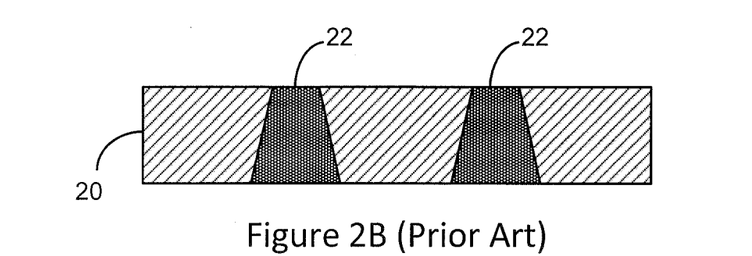
FIG. 2B is a cross-sectional view of the substrate in FIG. 2A after the laser-cut holes are filled with a metal from a metal paste.
Figure 3A:
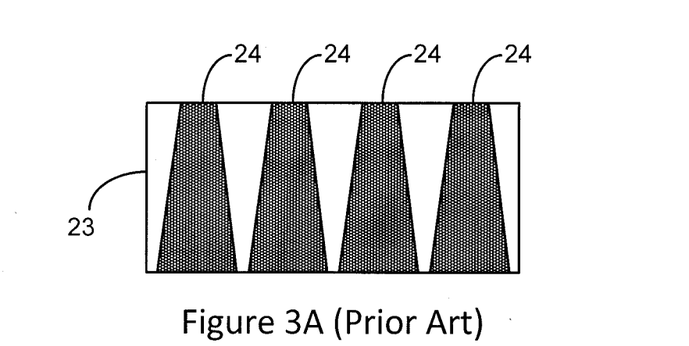
FIG. 3A is a cross-sectional view of an example thicker substrate produced by the method illustrated in FIGS. 2A-B illustrating, together with FIG. 3B the trade-off between substrate thickness (scalability) and hermeticity.
Figure 3B:
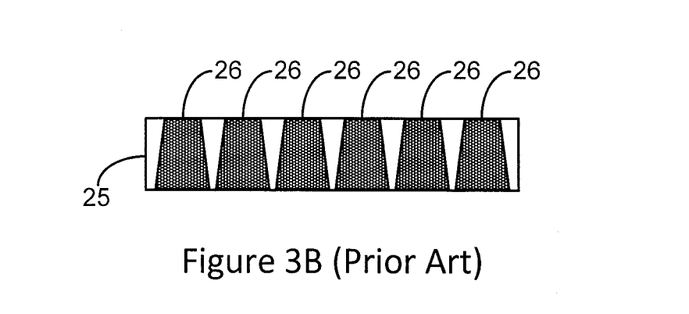
FIG. 3B is a cross-sectional view of an example thinner substrate produced by the method illustrated in FIGS. 2A-B illustrating, together with FIG. 3A the trade-off between substrate thickness (scalability) and hermeticity.

Various methods are known to produce hermetic electrically conducting feedthroughs. However, they often tend to be high-cost, lack scalability, and have inherent material incompatibilities. For example, FIGS. 2A and 2B illustrate a method for producing metal feedthroughs in laser drilled holes on non-conductive substrates. In this method, a ceramic or other electrically non-conductive substrate 20 is laser drilled with holes 21. The holes are turned into feedthroughs by filling them with thick-film metal paste 22 which consists of metal particles in an organic solvent. The metal paste is typically pulled through the holes using vacuum and fired at high temperature to drive out the solvent, leaving only metal in the holes. This method however can be problematic because the thick-film metal paste can leave voids when fired or the adhesion of metal to substrate may be poor, either of which can cause leakage paths through the feedthroughs leading to hermetic failure. Also the high-temperature firing can cause delamination of the metal from the ceramic due to the stresses induced from thermal expansion mismatch between the metal and the ceramic. And because hermetic package enclosures are typically made of bio-compatible metals which must be hermetically bonded to ceramic feedthrough substrates using a high temperature brazing process, this introduces an additional high temperature process which can further increase the chances of failure at the feedthrough-ceramic and also the ceramic-package interfaces. And the laser cutting process used to form holes can introduce additional limitations. For example, laser cutting can cause microcracks in the ceramic substrate, making it fragile and limiting the minimum gap between adjacent holes. And the minimum diameter of the substrate holes is restricted due to tapering produced by the laser cutting process which limits feedthrough density. As illustrated in FIGS. 3A and 3B, there exists a trade-off between substrate thickness (scalability) and hermeticity. Shorter holes (in which shorter feedthroughs 26 are formed) in thinner ceramic substrate 25 of FIG. 3B, are easier to laser cut, but they are less likely to be hermetic since there is a smaller area for the metal to adhere to the ceramic. Thicker ceramic substrates, such as 23 in FIG. 3A, provide more surface area for the metal to adhere and improve hermeticity. However, they are harder to laser cut, And as can be seen by the four longer feedthroughs 24 in FIG. 3A in the same substrate area as six shorter feedthroughs 26 in FIG. 3B, feedthrough density is less than a thinner substrate due to hole taper.

Figure 4A:
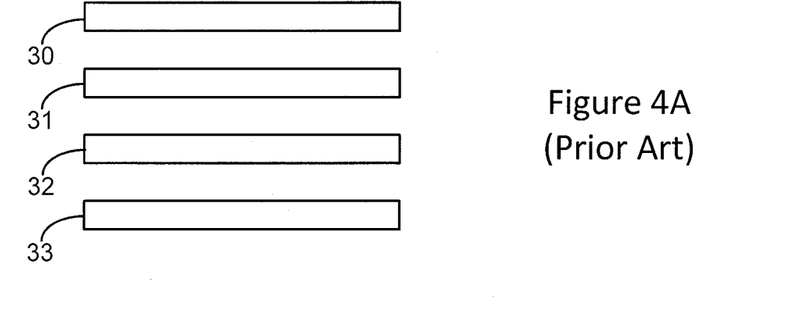
FIGS. 4A-D show four stages of a second example method of fabricating feedthroughs known in the art by co-firing multiple ceramic substrates.
Figure 4B:
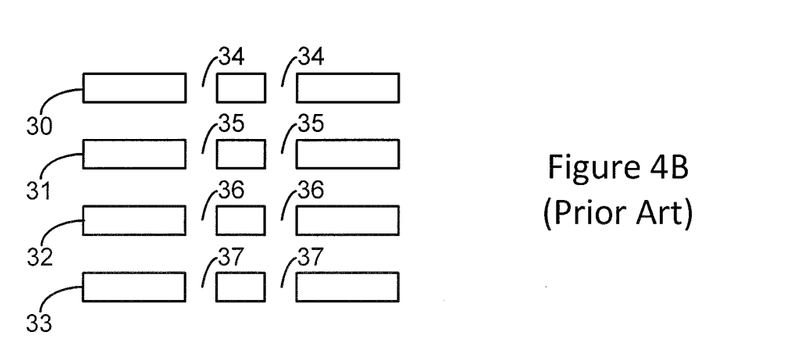
Figure 4C:
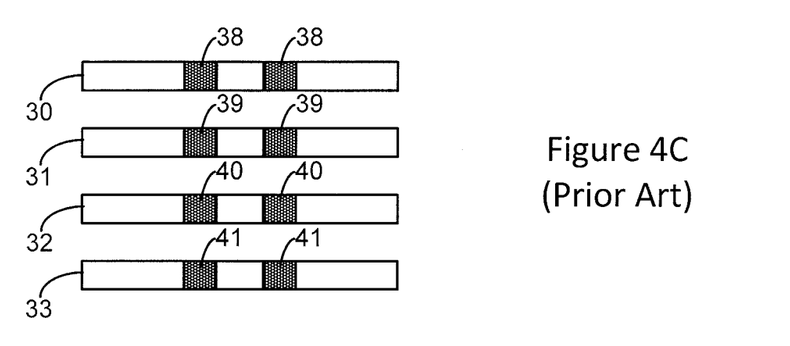
Figure 4D:
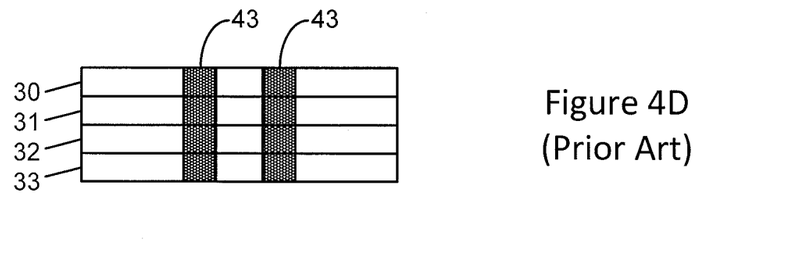

Another known method of producing hermetic electrically conducting feedthroughs uses co-fired multi-layer ceramics, and illustrated in FIGS. 4A-4D. In this method, multiple layers of thin ceramics 30-33 are physically punched with holes 34-37, respectively. Each ceramic layer 30-33 is then metalized using thick-film metal paste, 38-41, respectively, to create the feedthroughs in the holes. As shown in FIG. 4D, the layers of ceramics 30-33 are then stacked and co-fired to create the final substrate with feedthroughs 43 extending through the stack. However, the size of holes formed using this method is often restricted to the dimension of the punching process (e.g. about 100-125 microns). And the mechanical fragility of substrates due to punching can restrict the pitch between adjacent holes.

In order to improve the longevity and effectiveness of implantable devices, it is advantageous to be able to fabricate durable hermetic electrically conductive feedthroughs which allow connection to hermetically sealed electronic devices. In particular, it would be advantageous to provide a scalable fabrication method for producing high-density, bio-compatible, hermetic electrically conductive feedthroughs in a range of substrate thicknesses, that improves the hermetic bond between feedthrough and insulator by using lower temperature process for insulator sealing

SUMMARY

The technology described in this patent document includes devices, systems and methods for fabricating high-density hermetic electrical feedthroughs, and the feedthroughs produced thereby.

In one example implementation, a method of fabricating electrical feedthroughs is provided, comprising: coating each of a plurality of electrically conductive wires with an electrically insulating material; bundling the coated wires together in a substantially parallel arrangement; fixedly securing the bundled coated wires to each other by joining the electrically insulating material of adjacent wires together to form a monolithic block; and cutting the monolithic block transverse to the wires to produce a block section having opposing first and second sides with a plurality of electrically conductive feedthroughs extending therebetween.

In another example implementation, an electrical feedthrough substrate is provided, comprising: a substrate block having opposing first and second sides with a plurality of electrically conductive feedthroughs extending therebetween, wherein said electrically conductive feedthroughs are a plurality of electrically conductive wires each insulated with an electrically insulating material that is joined with adjacent electrically insulating material to fixedly secure the feedthroughs together in a substantially parallel arrangement without any gaps therebetween.

These and other implementations and various features and operations are described in greater detail in the drawings, the description and the claims.

DETAILED DESCRIPTION

The present invention is generally directed to a method of fabricating low-resistance, high-density, hermetic, preferably bio-compatible, electrical feedthroughs (or vias) using a plurality of bundled insulated wires that are fixedly secured to each other by joining (such as by co-firing/heating to melt) the insulator coatings of the wires together. The joining of the insulator material forms a gapless monolithic block which may be transversely cut into thinner block sections. For each block section, the wires extend between a first side and an opposite second side to form electrical feedthroughs (or vias). Additionally, contact pads may be formed on the opposing first and second sides so as to contact opposite ends of the same wire or wires.

It is notable that various types of electrically conductive materials may be used for the wires, especially materials having high electrical conductivity and stability in harsh environments. For bio-medical implant applications in particular, substrate materials that have high bio-compatibility and are capable of being hermetically sealed to implantable metal packages are preferred. Example bio-compatible electrically conductive substrate materials that may be used include: titanium and its alloys, such as surgical grade titanium —Ti6Al4V, Ti6Al4V ELI ('extra low interstitials') and niobium and alloys. While bio-compatible electrically conductive metal substrates are preferred in bio-medical implant applications, if the electrically conductive substrate material was further coated with an insulating material then any electrical conductor may be used, such as but not limited to platinum and alloys (such as platinum-iridium); iridium and alloys; ruthenium and alloys; Nitinol (Ti—Ni); palladium and alloys; rhodium and alloys, gold and alloys; copper and alloys, aluminum and alloys, surgical grade stainless steel such as 316LVM; p- or n-type doped silicon; etc. Electrical resistance of individual wires may be less than about 500 ohms. And it is also notable that various types of electrically insulating materials may be used as well, e.g. glass, polymer, or ceramic insulators. For example, the electrically insulating material may be a bio-compatible electrically insulating material, such as for example sealing glasses such as Pyrex, non-leaded glass, boro-silicate glass, glass-frit powder or paste, glasses or ceramics containing one or more of $B_2O_3$, CaO, BaO, $SiO_2$, $La_2O_3$, $Al_2O_3$, $Li_2O_3$, $TiO_2$.

Figure 5:
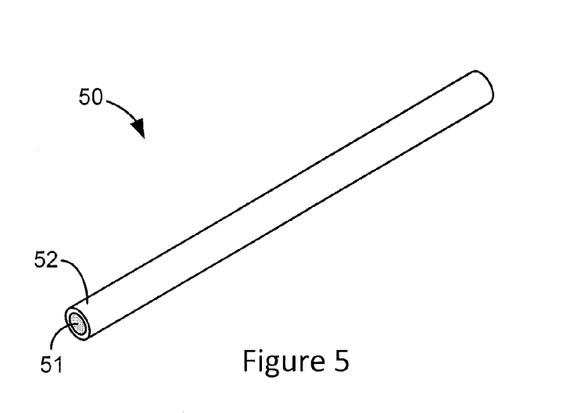
FIG. 5 is a perspective view of an individual wire coated with an insulating material, of the present invention.
Figure 6:
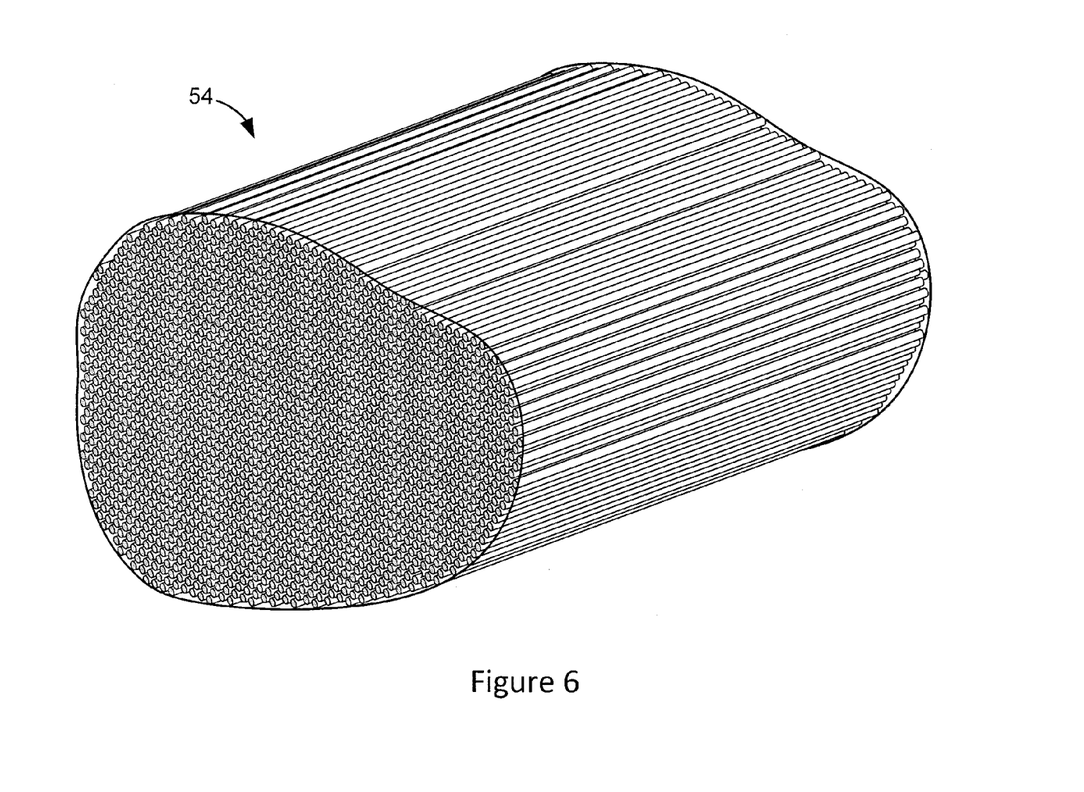
FIG. 6 is a perspective view of a plurality of coated wires bundled together, of the present invention.

Turning now to the drawings, FIG. 5 shows a single insulated wire construction 50 used to construct the electrically conductive feedthrough substrate and construction of the present invention. In particular, the insulated wire 50 has a generally elongated construction and includes an electrically conductive wire core 51 that is coated or otherwise surrounded with an electrically insulating material 52, using coating techniques known in the art. The electrically conductive wire diameters may range from about 0.01 μm to about 100 μm. And the electrically insulating material thickness may range from about 0.01 μm to about 300 μm. It is appreciated that while these are some typical example ranges suitable for many high density feedthrough applications, other ranges of wire diameter and insulator thickness are possible, such as for example from the nanoscale to mesoscale and higher ranges. And FIG. 6 shows a high-density bundle of insulated wires 54 created by joining a plurality of wires (such as 50 in FIG. 5) together in a manner that minimizes the voids and gaps between wires. The electrically insulating materials of the coated wires in this bundle may then be joined together to fixedly secure the wires together no that a monolithic block is formed having no gaps or voids.

Figure 10:
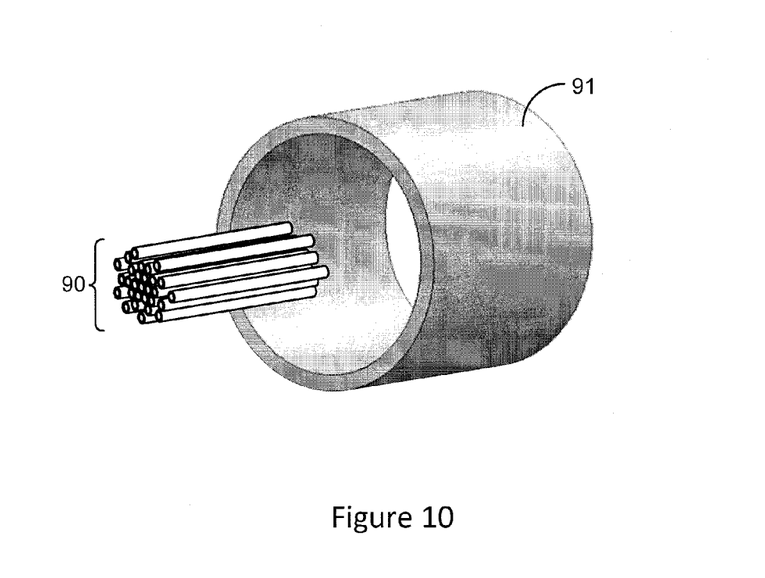
FIG. 10 is an exploded perspective view of another example embodiment of the electrically conductive feedthrough construction of the present invention where a plurality of insulated wires are inserted into and bundled by a ring-like structure, such as a metal ring.
Figure 11:
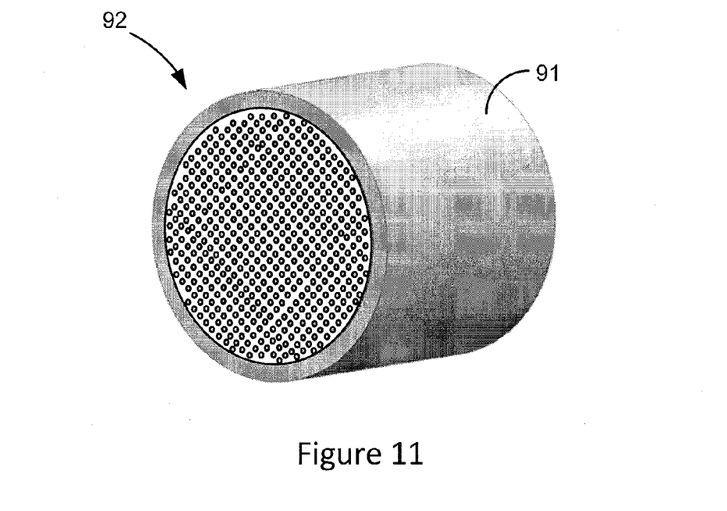
FIG. 11 is a perspective view of the example embodiment of and following FIG. 10 showing the monolithic substrate block thus formed.
Figure 12:
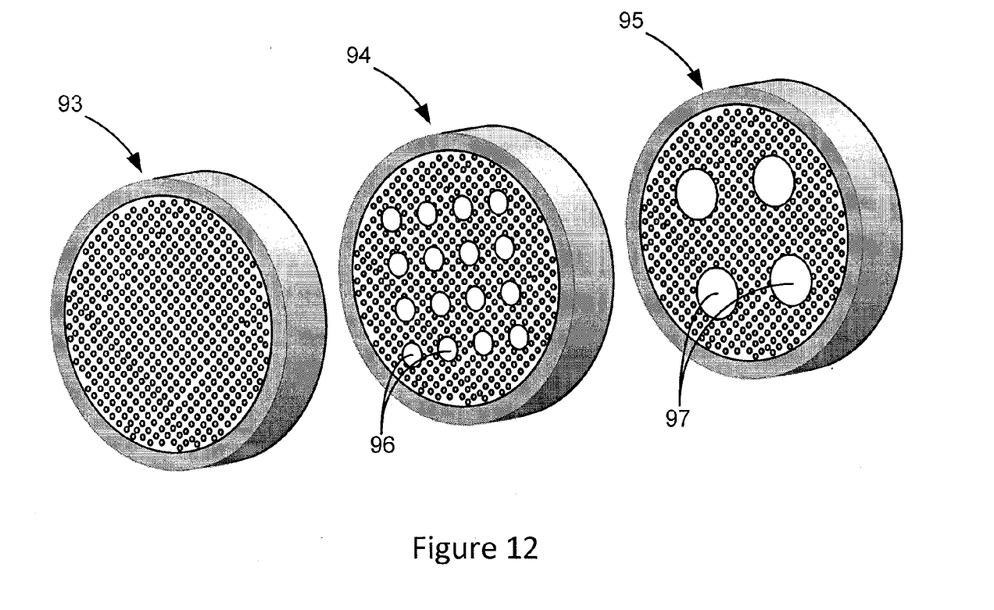
FIG. 12 is a perspective view of the example embodiment of and following FIG. 11 showing the multiple block sections formed by cutting the monolithic substrate block.

In one example embodiment, bundling of the wires may involve the use of various ties, straps, bands, or other binding structures and implements, such as for example a ring-like, annular band 91 shown in FIG. 10. As shown in FIG. 10, a plurality of insulated wires e.g. 90 is inserted into and surrounded by the annular ring 91, which may have a metal construction, for example. As used herein, a "ring-like structure" is a structure generally having a ring, tubular, or cylinder-wall configuration, but capable of various length-to-diameter (or height-to-diameter) aspect ratios such that a significantly high length-to-diameter aspect ratio produces what is typically considered a tube shape, whereas a significantly low height-to-diameter aspect ratio produces what is typically considered a conventional ring shape. And in FIG. 11, the resulting bundle may be co-fired together with the ring structure at high temperature to form the monolithic block 92. In FIG. 12, the monolithic block 92 is shown cut into thinner substrates, such as 93, 94, and 95. Each of these cut substrate block represents a substrate with an array of feedthroughs extending between opposing first and second sides. In particular, substrate 94 is shown having electrode contact pads 96 formed to create 16 feedthroughs, and substrate 95 is shown having electrode contact pads 97 formed to create 4 feedthroughs. An example range of the feedthrough thicknesses can be, for example, between about 50 um to about 5000 um, although no maximum limit. Each may be polished on both sides. The metal ring design of this embodiment makes the feedthrough substrate compatible for hermetic sealing to a metal package in further processing. It is notable that the"first side" is an arbitrary choice, since there is no distinction made in the claim between the first and second sides. And the electrically conductive pad formed on the first side of the block section and contacting the at least one feedthrough(s) is preferably accompanied by another corresponding electrically conductive pad formed on the second side of the block section and contacting the same at least one feedthrough(s) at the opposite end.

Figure 7:
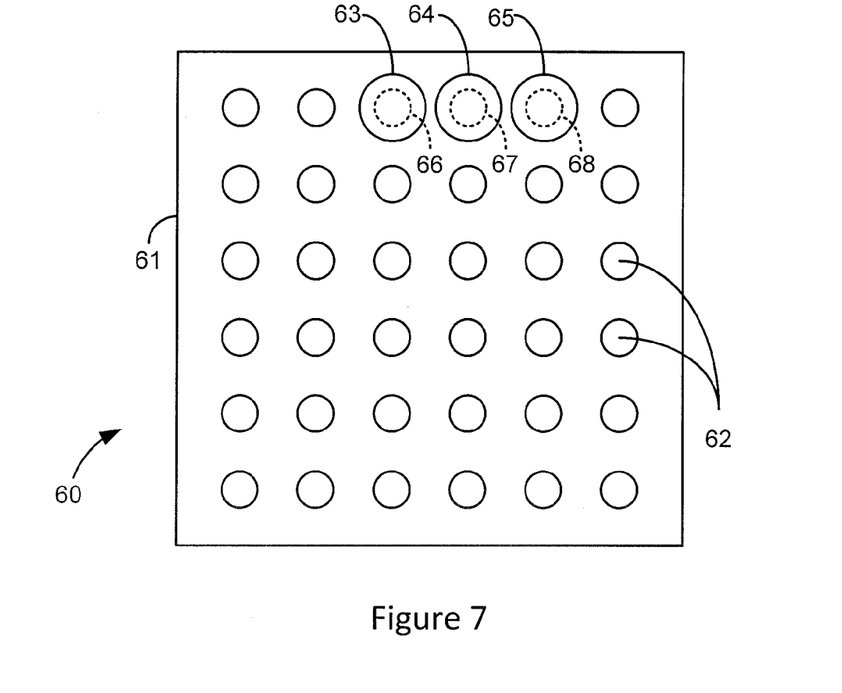
FIG. 7 is a top view of an example feedthrough substrate construction of the present invention having wires arranged in an ordered array with a geometrically repeating cross-sectional pattern, and showing single wires serving as single feedthroughs.

Based on the method of joining or assembling the wires, the resulting bundle or insulated wires may or may not be arranged in an ordered fashion. In particular, FIG. 7 shows a top view of an example feedthrough substrate construction 60 of the present invention having wires 62 arranged in an ordered array (surrounded by joined insulating material 61) with a geometrically repeating cross-sectional pattern, and showing single wires (e.g. 66-68) serving as single feedthroughs, as indicated by the one-to-one correspondence of contact pads 63-65 and wires 66-68, respectively. As shown in FIG. 7, if the insulated wires have a geometrically repeating pattern or arrangement, standard metal patterning techniques can be used to metalize the top and bottom of the substrate, i.e. form contact pads for electrodes. In this scenario, a single conducting wire may be used as a single feedthrough. However, additional wires may also be used per contact pad.

Figure 8:
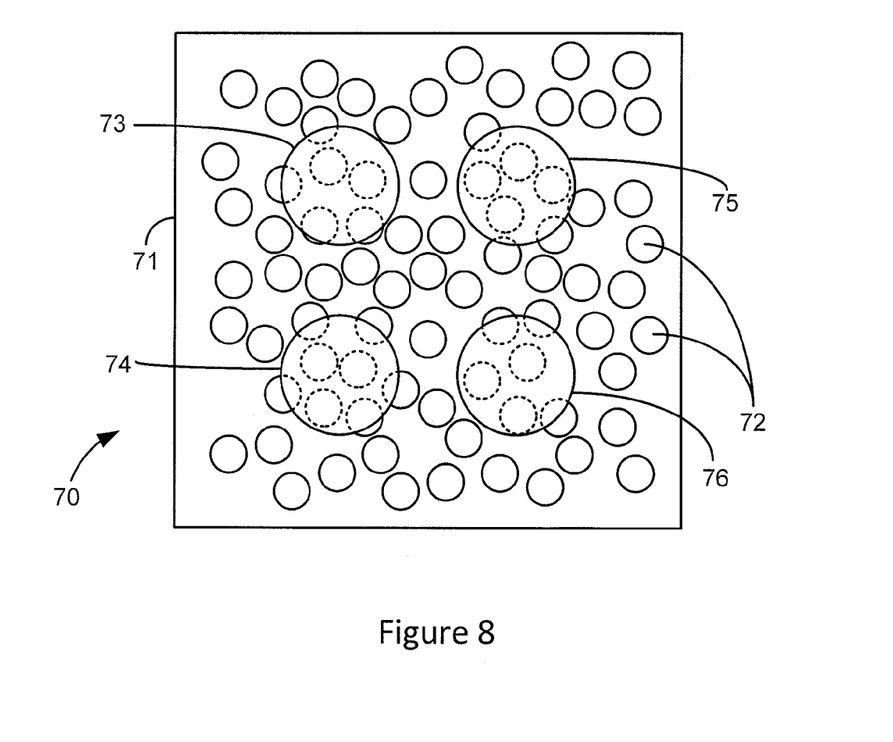
FIG. 8 is a top view of an example feedthrough substrate construction of the present invention having wires arranged in a randomly-ordered array not having a geometrically repeating cross-sectional pattern, and showing multiple wires serving as single feedthroughs.
Figure 9:
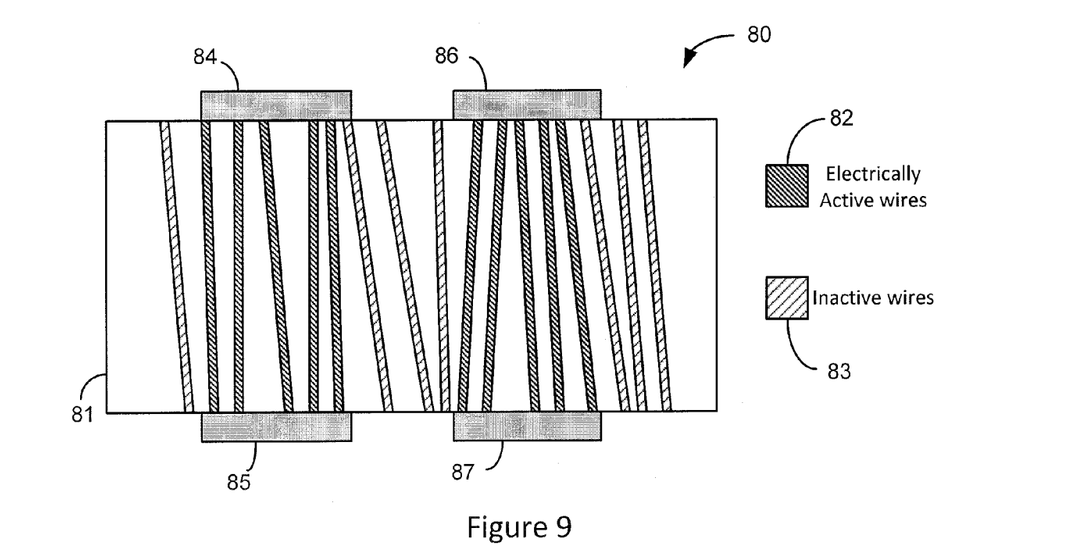
FIG. 9 is a cross-sectional view of an example feedthrough substrate construction of the present invention, similar to FIG. 8, and showing the connection of multiple electrically active wires between electrode pairs on opposite sides, and the non-use of inactive wires.

And FIG. 8 shows a top view of an example feedthrough substrate construction 70 of the present invention having wires 72 arranged in a randomly-ordered array not having a geometrically repeating cross-sectional pattern, and showing multiple wires serving as single feedthroughs, as represented by the multiple wires (broken lines) underneath contact pads 73-76. Similar to FIG. 7, the wires 72 are shown surrounded by joined insulating material 71. In this case, the insulated wires are randomly ordered and tapered, it would be difficult to use individual wires as feedthroughs because it would be necessary to map corresponding ends of each wire, so as to enable metal pads to be patterned on both sides of the substrate to contact the corresponding ends. Larger conductive pads that cover multiple (at least two) insulating wires can be used to create electrical feedthroughs, as shown in FIG. 8. Similarly, FIG. 9 shows a cross-sectional view of an example feedthrough substrate construction 80 of the present invention, similar to FIG. 8, and showing the connection of multiple electrically active wires between electrode pairs (e.g. 84-85, and 86-87) on opposite sides, and the non-use of inactive wires. In this case, multiple wires are patterned with a single metal pad. The electrically active wires are shown at 82 and the inactive wires are shown at 83. By measuring the average density of wires, and knowing the dimensions of the wire and insulator, the metal pads can be separated by a set gap such that there is no cross-talk between adjacent feedthroughs. In this case, an individual feedthrough consists of multiple wires.

In this manner, extremely high density of feedthroughs may be fabricated in the case of ordered wires. And in the case of non-ordered wires, alignment of the metal pads on the feedthroughs is not critical since multiple conducting wires form a single feedthrough. No dependence of hermeticity on substrate thickness. High and low aspect ratios of feedthroughs are possible without tapers typically seen in laser cutting processes. Existing methods are severely limited to the smallest pitch and diameters of the feedthrough holes that can be drilled. In this method, significantly thinner wires may be used to increase density.

It is notable that hermetically sealed packages with electrical feedthroughs is commonly used by many companies in the bio-medical device industry to separate non-bio-compatible components from bodily tissue. However, electrical feedthroughs are also heavily used in the semiconductor industry to interconnect electronic chips. And electrical feedthroughs may also be used in other applications, such as separating sensors or electronics from harsh environments in the field. It is appreciated therefore that while bio-compatible materials are preferred for use as one or both of the electrically conductive substrate/feedthroughs and electrically insulating materials of the present invention when used in bio-medical implant applications, other non-bio-compatible materials may be used in the alternative for other non-bio-medical applications. The challenge in all these applications, however, remains the same, that is to create very high-density hermetic feedthroughs using materials that are compatible with the environment of application.

Although the description above contains many details and specifics, these should not be construed as limiting the scope of the invention or of what may be claimed, but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

We claim:

1. A method of fabricating electrical feedthroughs, comprising:
    coating each of a plurality of electrically conductive wires with an electrically insulating material;
    bundling the coated wires together in a substantially parallel arrangement;
    fixedly securing the bundled coated wires to each other by joining the electrically insulating material of adjacent wires together to form a monolithic block; and
    cutting the monolithic block transverse to the wires to produce a block section having opposing first and second sides with a plurality of electrically conductive feedthroughs extending therebetween,
    wherein the bundled coated wires are fixedly secured as a randomly-ordered array not having a geometrically repeating cross-sectional pattern.

2. The method of claim 1,
wherein the electrically conductive wires are a bio-compatible metal.

3. The method of claim 1,
wherein the electrically insulating material is selected from the group consisting of glass, polymer, ceramic, and other dielectric materials.

4. The method of claim 1,
wherein the electrically insulating material is a bio-compatible material.

5. The method of claim 1,
further comprising forming a first electrically conductive contact pad on the first side of the block section to contact a first end of at least two of the wires, and a second electrically conductive contact pad on the second side of the block section to contact an opposite second end of the same wires.

6. The method of claim 1,
wherein the coated wires are bundled together with a ring-like structure surrounding the coated wires.

7. The method of claim 1,
wherein the electrically insulating material of adjacent wires are joined together by being heated at elevated temperatures.

8. An electrical feedthrough substrate, comprising:
a substrate block having opposing first and second sides with a plurality of electrically conductive wires extending therebetween, wherein said electrically conductive wires are each insulated with an electrically insulating material that is joined with electrically insulating material of adjacent wires to fixedly secure the wires together in a substantially parallel arrangement without any gaps therebetween,
wherein the electrically conductive wires are arranged in a randomly-ordered array not having a geometrically repeating cross-sectional pattern.

9. The electrical feedthrough substrate of claim 8,
wherein the electrically conductive wires are a bio-compatible metal.

10. The electrical feedthrough substrate of claim 8,
wherein the electrically insulating material is selected from the group consisting of glass, polymer, ceramic, and other dielectric materials.

11. The electrical feedthrough substrate of claim 8,
wherein the electrically insulating material is a bio-compatible material.

12. The electrical feedthrough substrate of claim 8,
further comprising a first electrically conductive contact pad on the first side of the substrate block contacting a first end of at least two of the wires, and a second electrically conductive contact pad on the second side of the substrate block contacting an opposite second end of the same wires.

13. The electrical feedthrough substrate of claim 8,
wherein the substrate block includes a ring-like structure surrounding the plurality of electrically conductive wires and joined electrically insulating material.

* * * * *